US006469058B1

(12) United States Patent
Grove et al.

(10) Patent No.: US 6,469,058 B1
(45) Date of Patent: Oct. 22, 2002

(54) CHEMOTHERAPY OF CANCER WITH ACTYLDINALINE IN COMBINATION WITH GEMCITABINE CAPECITABINE OR CISPLATIN

(75) Inventors: William Richard Grove, Whitmore Lake, MI (US); Wayne Daniel Klohs, Ypsilanti, MI (US); Ronald Lynn Merriman, Ann Arbor, MI (US)

(73) Assignee: Warner-Lambert Company, Morris Plains, NJ (US)

( * ) Notice: Subject to any disclaimer, the term of this patent is extended or adjusted under 35 U.S.C. 154(b) by 0 days.

(21) Appl. No.: 09/744,130

(22) PCT Filed: Jul. 8, 1999

(86) PCT No.: PCT/US99/15386

§ 371 (c)(1),
(2), (4) Date: Jan. 19, 2001

(87) PCT Pub. No.: WO00/18393

PCT Pub. Date: Apr. 6, 2000

Related U.S. Application Data (60) Provisional application No. 60/101,809, filed on Sep. 25, 1998.

(51) Int. Cl.[7] .................... A01N 55/02; A01N 37/18; A61K 31/28; A01K 31/16
(52) U.S. Cl. .................... 514/492; 514/449; 514/616; 514/219
(58) Field of Search .................... 514/492, 616, 514/449, 219

(56) References Cited

U.S. PATENT DOCUMENTS 5,137,918 A * 8/1992 Weiershausen et al. ..... 514/616

FOREIGN PATENT DOCUMENTS

WO    WO98/47500    10/1998

OTHER PUBLICATIONS van Moorsel et al. "Combination chemotherapy studies with gemcitabine" (abstract), 1997.*

Physicians Desk Reference (p. 1482) (1997).*

"Clinical Development of Novel Therapeutics" Karmanos Cancer Institute (1996–2001).*

A. Graul, et al., "Antineoplastic", Drugs of the Future, Nov. 1997, pp. 1201–1204, vol. 22, No. 11.

H. Schaider, et al., "Combination Treatment Based on Metabolic Effects od Dinaline", J Cancer Res Clin On col, 1995, pp. 203–210, vol. 121, No. 4.

T. Corbett, et al., "Tumor Models and the Discovery and Secondary Evaluation of Solid Tumor Active Agents", Inatl J Pharm, 1995, pp. 102–122, vol. 33, Suppl.

C. T. Howard, et al., "In Vivo Antitumor Activity of CI–994 Alone and in Combination with Gemcitabine Against LC12 Squamos Cell Lung Carcinoma", Proc American Assoc Can Res Annual Meeting, Mar. 1999, pp. 590, vol. 40.

* cited by examiner

Primary Examiner—Jose' G. Dees
Assistant Examiner—Robert DeWitty
(74) Attorney, Agent, or Firm—Charles W. Ashbrook; Rosanne Goodman; Steven R. Eck (57) ABSTRACT

Acetyldinaline in combination with gemcitabine, a pharmaceutically acceptable salt thereof, capecitabine, or cisplatin is synergistic for treating cancer.

11 Claims, 6 Drawing Sheets

FIG-1 EFFECT OF CI-994 AGAINST LC12 SQUAMOUS CELL LUNG CARCINOMA

FIG-2  EFFECT OF GEMCITABINE AGAINST LC12 SQUAMOUS CELL LUNG CARCINOMA

FIG-6  CI-994 / CisPt COMBINATION IN OVCAR - 4 CELLS

CHEMOTHERAPY OF CANCER WITH ACTYLDINALINE IN COMBINATION WITH GEMCITABINE CAPECITABINE OR CISPLATIN

This application claims the benefit of provisional application No. 60/101,809, filed Sep. 25, 1998.

FIELD OF THE INVENTION

The invention concerns a method for treating tumors utilizing a combination of known oncolytic agents. The use of the agents together provides unexpectedly greater efficacy than employing the single agents alone.

BACKGROUND OF THE INVENTION

Cancer chemotherapy has advanced dramatically in recent years. Many tumors can be effectively treated utilizing compounds which are either naturally occurring products or synthetic agents. Cancer chemotherapy often entails use of a combination of agents, generally as a means of providing greater therapeutic effects and reducing the toxic effects that are often encountered with the individual agents when used alone.

We have now discovered a unique combination of known oncolytic agents which exhibits a dramatic synergistic effect. The combination utilizes the agent acetyldinaline, together with either gemcitabine, capecitabine, or cisplatin. The combination is especially effective in treating patients with solid tumors, especially nonsmall cell lung cancer and other advanced solid tumors.

Acetyldinaline is 4-acetylamino-N-(2'-aminophenyl)-benzamide. It is also known as CI994. It is described in U.S. Pat. No. 5,137,918, which is incorporated herein by reference for its teaching of how to make acetyldinaline, how to formulate it into dosage forms, and how to use it for treating cancers such as colon cancer and adenocarcinomas. It is also described in U.S. Pat. No. 5,795,909 as a possible conjugate for cancer treatment.

Gemcitabine is the generic name assigned to 2'-deoxy-2', 2'-difluoro-cytidine. It is commercially available as the monohydrochloride salt, and as the β-isomer. It is also known chemically as 1-(4-amino-2-oxo-1H-pyrimidin-1-yl)-2-desoxy-2,2-difluororibose. Gemcitabine is disclosed in U.S. Pat. Nos. 4,808,614 and 5,464,826, which are incorporated herein by reference for their teaching of how to synthesize, formulate, and use gemcitabine for treating susceptible neoplasms. The commercial formulation of gemcitabine hydrochloride is indicated as first-line treatment for patients with locally advanced (nonresectable Stage II or Stage III) or metastatic (Stage IV) adenocarcinoma of the pancreas, and is commonly used in patients previously treated with 5-fluorouracil.

Capecitabine is a fluoropyrimidine carbamate with antineoplastic activity. It is an orally administered systemic prodrug of 5'-deoxy-5-fluorouridine (5'-DFUR) which is converted to 5-fluorouracil. The chemical name for capecitabine is 5'-deoxy-5-fluoro-N-[(pentyloxy)carbonyl]-cytidine. It is marketed in the United States as Xeloda™ (Roche Laboratories). It is indicated for the treatment of patients with metastatic breast cancer and colorectal tumors. It generally is administered for 14 days, followed by a 7-day rest period during each 21-day cycle. Capecitabine is described in U.S. Pat. No. 5,472,949.

Cisplatin is the generic name for cis-diaminodichloroplatinum and is described in U.S. Pat. No. 5,562,925, which is incorporated herein by reference. Cisplatin is commercially available and is indicated for metastatic testicular and ovarian tumors, as well as advanced bladder cancer.

An object of this invention is to provide a method for treating cancers, especially advanced solid tumors. with a combination comprising acetyldinaline together with either gemcitabine, capecitabine, or cisplatin. A further object is to provide a composition comprising synergistic amounts of acetyldinaline and gemcitabine, synergistic amounts of acetyldinaline and capecitabine, and synergistic amounts of acetyldinaline and cisplatin.

SUMMARY OF THE INVENTION

This invention relates to a synergistic combination of antineoplastic agents, and to a method for treating tumors comprising administering the combination. The invention more particularly provides a composition comprising, as a first component, acetyldinaline, and as a second component, either gemcitabine, capecitabine, or cisplatin. The gemcitabine is used preferably as a pharmaceutically acceptable acid addition salt.

The compositions of this invention consist essentially of the above active ingredients, or suitable salts thereof, together with common excipients, diluents, and carriers.

A preferred composition comprises acetyldinaline, together with gemcitabine hydrochloride. Another preferred combination is acetyldinaline and cisplatin.

In a further embodiment of the invention, we provide a method for treating cancer comprising administering to an animal in need of treatment an effective amount of a combination of acetyldinaline and either cisplatin, or gemcitabine, preferably as a salt such as the hydrochloride.

A preferred method embraces treatment of solid tumors.

A further preferred method employs an antitumor amount of acetyldinaline and an effective amount of gemcitabine hydrochloride, capecitabine, or cisplatin to treat susceptible cancers, including nonsmall cell lung cancer (NSCLC), breast cancer, ovarian cancer, head and neck cancer, myelomas, prostate cancer, and pancreatic cancer.

Another embodiment of the invention is a kit comprising in one compartment a dosage of acetyldinaline, and in another compartment a dosage of gemcitabine, or a pharmaceutically acceptable salt thereof. A further embodiment is a kit comprising in one compartment a dosage of acetyldinaline, and in another compartment a dosage of capecitabine or cisplatin.

DETAILED DESCRIPTION OF THE INVENTION

The compounds to be utilized in the method of this invention will be administered in doses commonly employed clinically. Such doses will be calculated in the normal fashion, for example on body surface area. Acetyldinaline will be administered, for example, at doses from about 1.0 mg/m² to about 50 mg/m², preferably from about 2.0 mg/m² to about 10.0 mg/m². Ideally, acetyldinaline will be administered at a dose which will produce plasma levels of about 5 to about 100 $\mu$/mL. Acetyldinaline typically is administered orally, for example. as capsules having active ingredient in the amounts of 2.5, and 25 mg per capsule. Acetyldinaline will be administered daily at about the same dose levels throughout a treatment period, typically for 15 to 30 days. Multiple treatment periods can be practiced, as dictated by the attending medical practitioner and the particular patient and condition being treated.

Gemcitabine will likewise be administered at doses comparable to those routinely utilized clinically. For example, the initial dose of gemcitabine, typically as the hydrochloride salt, will be about 1000 mg/m² of body surface area. This product is routinely formulated as a sterile solution and is administered by intravenous infusion, generally over about a 30-minute period, with about 2 to 4 weekly doses, with courses repeated about every 28 to 30 days. The dose of 1000 mg/m² can be given for up to about 7 weeks, according to this treatment regimen, or until undesirable side effects are observed. Other salt forms can be utilized if desired, for example, the hydrobromide, monophosphate, sulfate, malonate, citrate, and succinate are readily prepared.

Capecitabine for monotherapy generally is administered orally at a dose of about 2500 mg/m² daily for 2 weeks, followed by a 1-week rest period. The product is supplied commercially in 150 mg and 500 mg tablets. The tablets are administered at the rate of about 1 to about 4 times a day during the treatment period. The daily doses of capecitabine will range from about 1000 mg/m² to about 3500 mg/m² per day in the combinations of this invention.

Cisplatin generally is formulated as a sterile solution for injection, and is routinely administered at doses of about 10 to 100 mg/m², given intravenously on a daily basis for about 5 to 6 days. Alternatively, cisplatin may be administered as a single dose of about 50 to 100 mg/m². This cycle can be repeated for about every 4 to 8 weeks.

The combinations provided by this invention have been evaluated in several assay systems, and the data can be analyzed utilizing a standard program for quantifying synergism, additivism, and antagonism among anticancer agents. The program preferably utilized is that described by Chou and Talalay, in "New Avenues in Developmental Cancer Chemotherapy," *Academic Press,* 1987, Chapter 2.

The method is based on the median-effect principle of the mass-action law using an enzyme kinetic system as a model. The equation is simple and describes the relationships between dose and effect regardless of the shape of the dose-effect curve. Two basic equations constitute the pillars of this methodology. To relate dose and effect for a single drug in the simplest way possible, the median-effect equation derived by Chou is given by:

$$f_a/f_u = (D/D_m)^m$$

$$D = D_m[f_a/(1-f_a)]^{1/m}$$

where the right side represents the dose and the left side represents the effect, in which $f_a$ and $f_u$ are the fractions affected and unaffected, respectively. D is the dose, $D_m$ is the median-effect dose signifying the potency, and m is a coefficient signifying the shape of the dose-effect curve. From this equation Chou and Talalay derived the general equation for two or more drugs:

$$\left[\frac{(f_a)_{1,2}}{(f_u)_{1,2}}\right]^{1/m} = \left[\frac{(f_a)_1}{(f_u)_1}\right]^{1/m} + \left[\frac{(f_a)_2}{(f_u)_2}\right]^{1/m} =$$

$$+\alpha\left[\frac{(f_a)_1(f_a)_2}{(f_u)_1(f_u)_2}\right]^{1/m} = \frac{(D)_1}{(D_m)_1} + \frac{(D)_2}{(D_m)_1} = \frac{\alpha(D)_1(D)_2}{(D_m)_1(D_m)_2}$$

where m−1 is for first-order Michaelis-Menten-type kinetics and m >1 (or m <1) is for higher order (or lower order) Hill-type kinetics. When alpha =0, the third term on the right side disappears and when alpha=1. the third term is conserved. Alpha =0 is used for mutually exclusive drugs and alpha=1 is used for mutually nonexclusive drugs. For drugs that have the same or similar modes of action, the effects of both drugs are mutually exclusive. For drugs that have different modes of action or act independently, the effects of both drugs are mutually nonexclusive.

A plot of fraction affected ($F_a$) versus combination index (CI) is called the $F_a$-CI plot. This plot indicates synergism, additivity, or antagonism of two drugs at various effect levels in a mixture that is serially diluted. If several mixtures are made, it is possible to estimate the optimal combination ratio for maximal synergy. Different effect levels usually give different degress of synergism, additivism, or antagonism. CI values <1 indicate synergism; CI values >1 indicate antagonism, and CI values that are one or hover around one indicate additivity. For anticancer agents, synergism at high effect levels ($F_a$) is clinically more relevant than synergism at low $F_a$ levels.

Gemcitabine, as the monohydrochloride, is routinely used clinically, and is well-suited as a single agent as a front-line treatment of patients with advanced pancreatic cancer or NSCLC. It also is routinely used in combination with other known antineoplastic agents, most notably cisplatin. No synergistic combinations have, however. heretofore been reported.

While acetyldinaline (CI-994) has not been approved for clinical use, it has nevertheless been evaluated in several clinical trials. In one such study, patients were treated using a dose-escalation scheme that increased both the daily dose and the duration of treatment. The majority of patients had received extensive prior chemotherapy. The maximum tolerated dose (MTD) was 15 mg/m²/day when the duration of treatment was 14 consecutive days. To allow more prolonged treatment, lower doses were studied. Using a schedule of 8 weeks of continuous daily therapy, followed by a 2-week 'drug holiday', the MTD was 8 mg/m²/day. The dose-limiting toxicity was thrombocytopenia or neutropenia, usually occurring within 1 month of the start of therapy. Blood counts tended to stabilize even with continued treatment and to recover quickly when treatment was stopped. There was no evidence of cumulative toxicity following repeated courses and prolonged exposures to CI-994. Other toxicities included nausea, vomiting, diarrhea, anorexia, fatigue, mucositis, headache, dehydration, and increases in liver and renal function test values. Responses included one partial response in a heavily pretreated patient with NSCLC and a minor response in one patient each with renal cell cancer and NSCLC.

An additional Phase 1 study was conducted in patients with relapsed acute leukemia or other hematologic malignancy using a once daily high-dose 5-day dosing schedule. The MTD was 135 mg/m$^2$/day. The dose-limiting toxicity was acute CNS toxicity manifested as sedation and somnolence. Other adverse events included nausea, vomiting, hypotension resulting from dehydration, hypocalcemia, headache, and in one patient each, acute pancreatitis, a pyramidal syndrome characterized by hyperreflexia and bilateral Babinski reflexes, and sepsis. Hematologic toxicities cannot be assessed in this patient population. Two patients with AML developed tumor lysis syndrome, resulting in one death. Transient decreases in peripheral white blood cell counts were noted.

A Phase 2 program is currently being conducted with CI-994, used as a single agent. The dosing regimen is 8 mg/m$^2$ given orally daily. Over 100 patients have been treated, including patients with nonsmall cell lung cancer, renal cell cancer, pancreatic cancer, head and neck cancer, ovarian cancer, myeloma, prostate cancer, and breast cancer. Some patients have tolerated dose increases to 10 mg/m$^2$, while some patients have had to have treatment interrupted due to thrombocytopenia, and then be restarted on CI-994 at lowered doses. The adverse events have been similar to those observed in the chronic dosing Phase 1 protocol. Thrombocytopenia has been the dose-limiting toxicity. Infrequent neurologic adverse events including paresthesias, confusion, and hallucinations have been reported. Objective responses have been seen in patients with nonsmall cell lung cancer. Clinical benefit has been reported in patients with renal cell cancer.

In the solid tumor Phase 1 study, CI-994 doses were administered orally following a fasting period, and blood samples were collected for pharmacokinetic analyses. Preliminary results indicate that the maximum blood level is achieved approximately 1 to 2 hours after ingestion, and the terminal elimination half-life of CI-994 is approximately 15 hours. The maximum plasma CI-994 concentrations achieved with increasing dose levels were less than dose-proportional. The terminal elimination half-life and the apparent clearance rate were independent of the dose administered.

One additional objective of this study was to determine whether taking CI-994 with food affected its rate or degree of absorption. Twelve fasted patients were given a single dose of CI-994, 8 mg/m$^2$. One week later, the same patients were given the same dose of CI-994 with a normal meal. Analysis of pharmacokinetic data revealed that CI-994 can be taken without regard to meals.

Mass balance/route of elimination studies have not been conducted in humans. Animal studies indicate that the principal route of elimination is via renal excretion, with 80% and 62% of radiolabeled drug appearing in the urine of monkeys and rats, respectively, within 24 hours.

The following detailed examples further establish the synergy between CI-994 and either gemcitabine, capecitabine, or cisplatin.

EXAMPLE 1

The synergistic combinations provided by this invention have been evaluated in standard chemotherapy studies using female BALB/C mice weighing 18 to 20 grams. On Day 0 of the test, each mouse was surgically implanted (subcutaneously) with a fragment of LC-12 squamous cell lung carcinoma tumor weighing approximately 30 mg. The mice were weighed weekly, and tumor size (width and length in mm) were measured three times each week with standard calipers. Tumor mass for each animal was calculated according to the formula:

$$\text{mass} = \frac{(a \times b^2)}{2},$$

where "a" is width of the tumor in mm, and "b" is the length in mm. Evaluation of anticancer activity was established by the formula T-C, where "T" and "C" are the median time (in days) required for the treated and control (respectively) tumors to reach a pre-determined size of 750 mg (the "evaluation size"). Acetyldinaline was suspended in 0.5% aqueous methyl cellulose and administered orally at various dosages in 0.5 mL volumes. Gemcitabine hydrochloride was dissolved in 5% aqueous saline and administered intraperitoneally at various dosage levels in 0.5 ml, injections.

Figure 1:
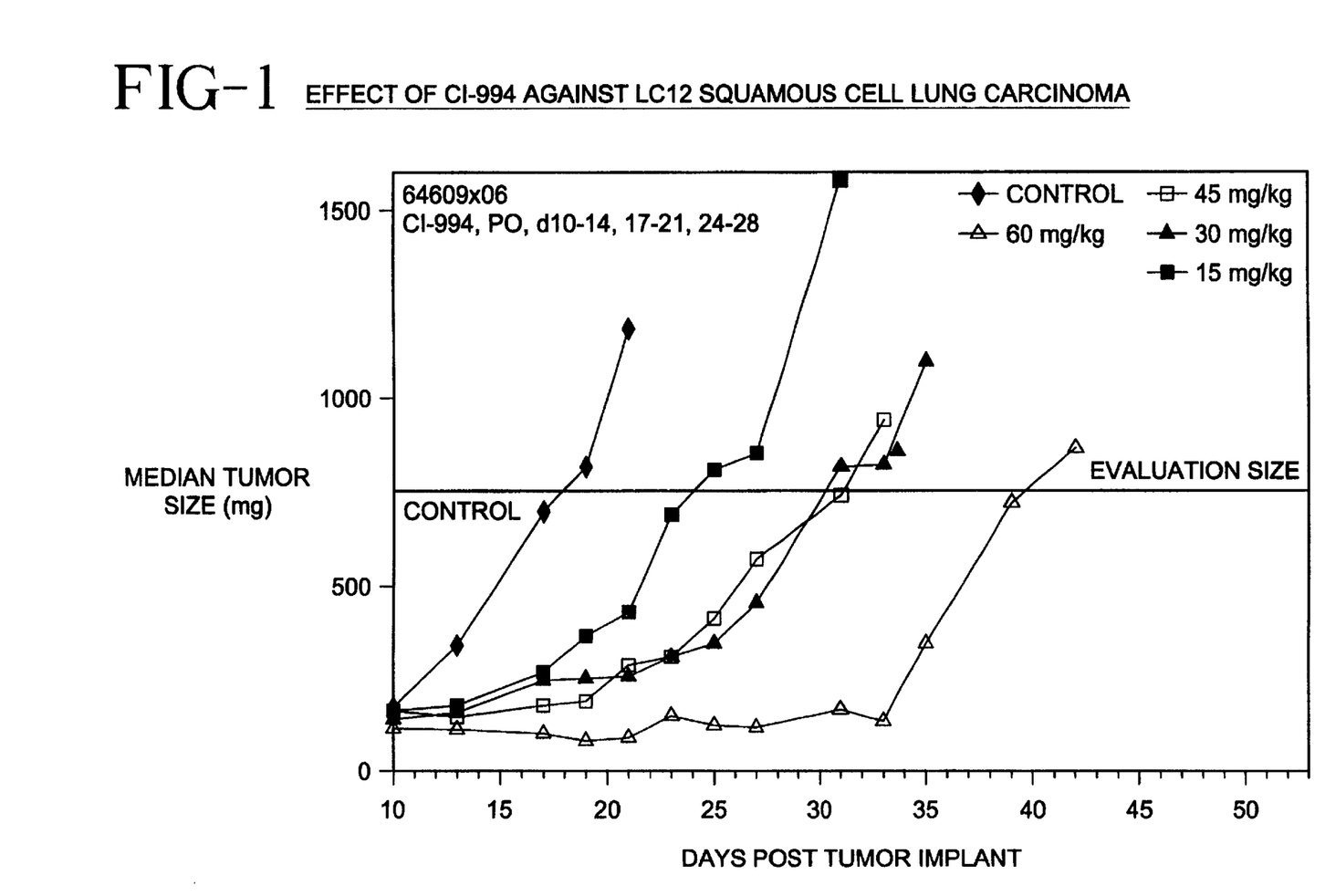
FIG. 1 shows the reduction in the rate of growth of transplanted tumors in mice following various oral doses of acetyldinaline (CI-994).

The animals were divided into four groups. One group served as controls and received no drug treatments. One group (FIG. 1) was further divided into four sub-groups, each of which received oral doses of acetyldinaline at a specified level of active drug (15 mg/kg, 30 mg/kg, 45 mg/kg, and 60 mg/kg). The acetyldinaline was administered daily on Days 10–14 (Day 0 being when the tumor was implanted), Days 17–21, and Days 24–28. FIG. 1 shows that acetyldinaline delays the growth of the implanted tumor at all dose levels, relative to untreated controls. Tumors in untreated controls exhibited significant growth, starting on Day 10. At the 30 and 45 mg/kg dosages of acetyldinaline, significant tumor growth did not commence until about Day 24. At 60 mg/kg, growth was delayed for 33 days.

Figure 2:
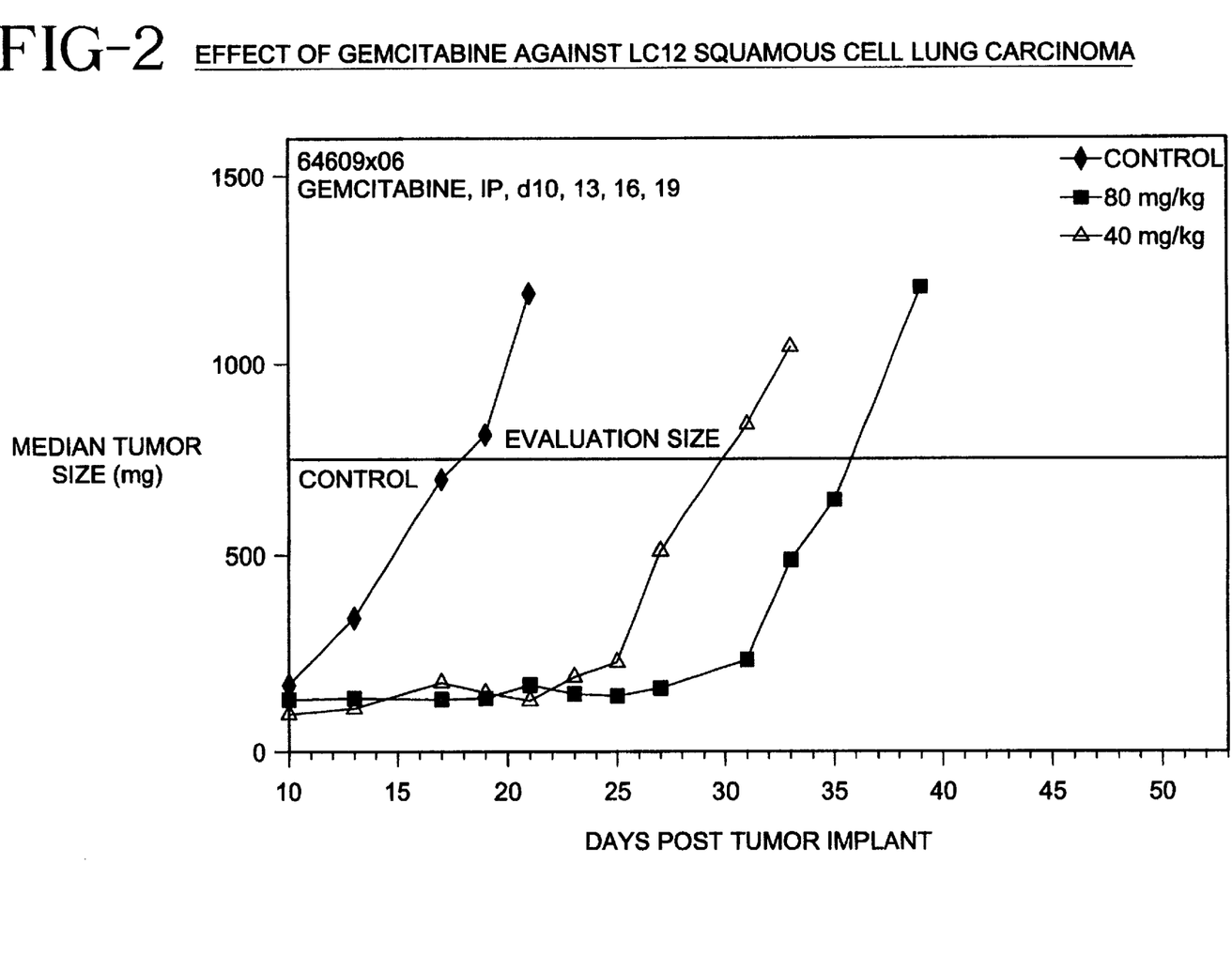
FIG. 2 shows the reduction in the rate of growth of transplanted tumors in mice following various interperitoneal injections of gemcitabine hydrochloride.

FIG. 2 shows the effects of gemcitabine hydrochloride at 40 and 80 mg/kg, administered IP on Days 10, 13, 16, and 19. Tumor growth was substantially inhibited for 25 days at 40 mg/kg, and for about 32 days at 80 mg/kg. (Controls showed significant growth starting at Day 10.)

Figure 3:
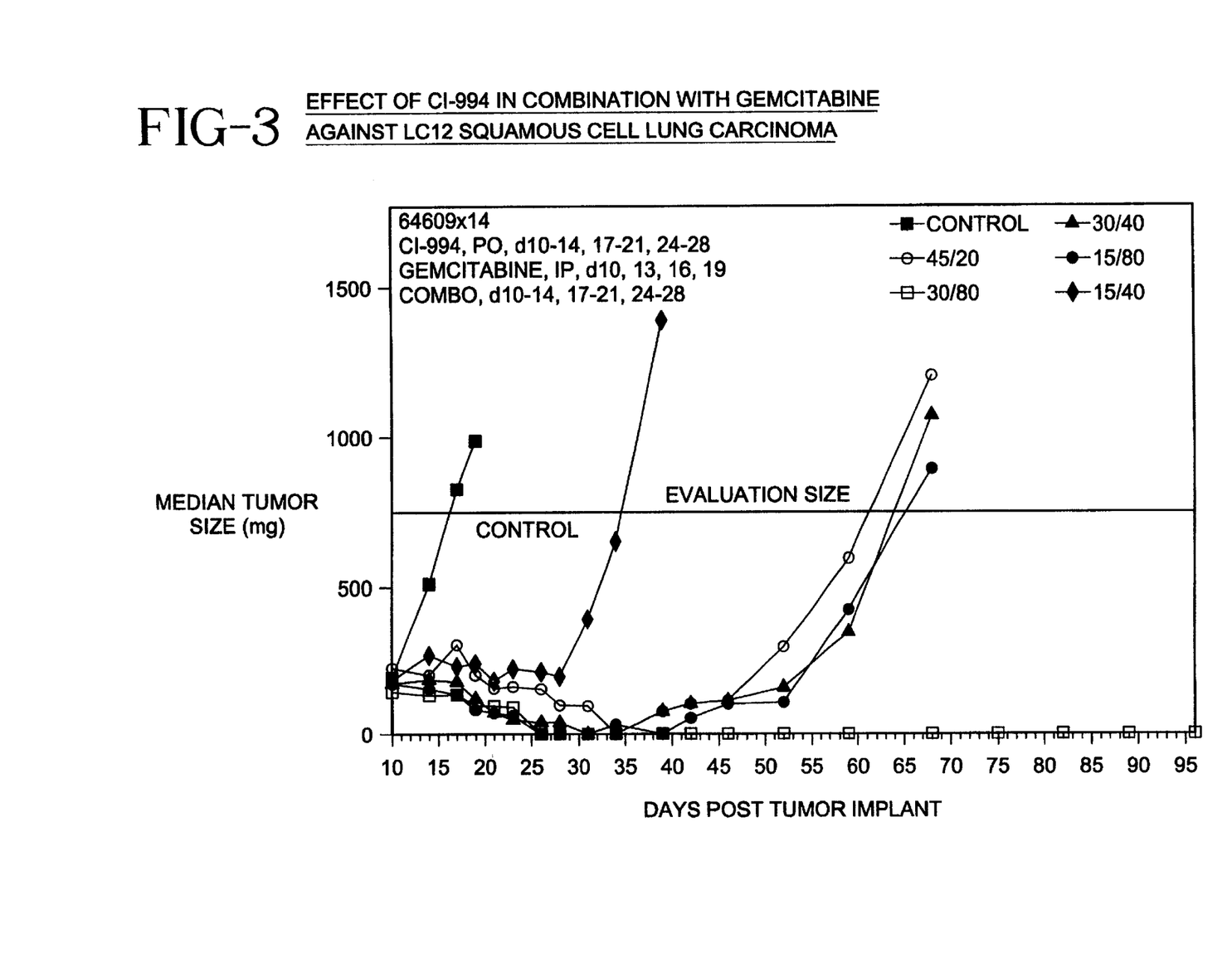
FIG. 3 shows the reduction in the rate of growth of transplanted tumors in mice following various dose combinations of acetyldinaline and gemcitabine hydrochloride (both agents given at the same time).

FIG. 3 shows the effects of various dose combinations of acetyldinaline and gemcitabine hydrochloride (e.g., 15 mg/kg of acetyldinaline with 40 mg/kg gemcitabine hydrochloride 15/80, 30/40, 30/80, and 45/20). The test animals were implanted with an LC12 squamous cell lung carcinoma, and were divided into four sub-groups, each sub-group receiving a different dosage of combination therapy. Acetyldinaline was administered orally at the indicated dosages on Days 10–14 (e.g., 15 mg/kg daily), Days 17–21, and Days 24–28. The gemcitabine hydrochloride was administered IP on Days 10, 13, 16, and 19. The results in FIG. 3 establish a dramatic and synergistic reduction in tumor growth for all combination doses of drugs. At the combination of 15 mg/kg acetyldinaline and 40 mg/kg gemcitabine, no substantial growth of the implanted tumor occurred until Day 28 (tumors in controls started substantial growth on Day 10). At combination doses of 15/80, 30/40, 30/80, and 45/20 (acetyldinaline/gemcitabine), tumor growth was substantially inhibited for the full 60-day period of the test.

Figure 4:
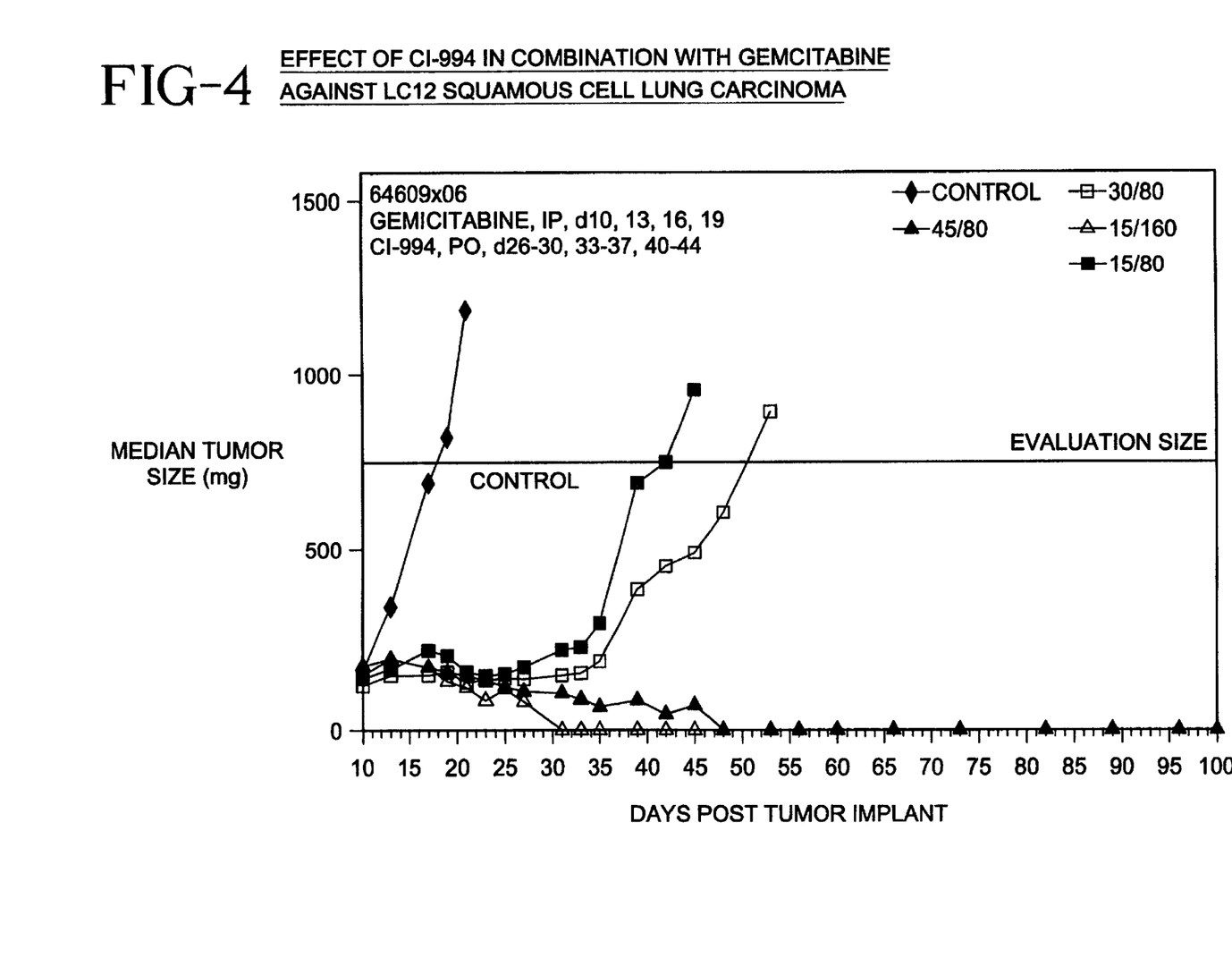
FIG. 4 shows the reduction in the rate of growth of transplanted tumors in mice following various dose combinations of acetyldinaline and gemcitabine hydrochloride (gemcitabine is given first, followed by dosing with CI-994).

FIG. 4 shows the results of a combination study carried out for 75 days. All test animals were implanted with an LC12 squamous cell lung carcinoma. Animals selected to receive test drugs were divided into four sub-groups. One sub-group received 15 mg/kg of acetyldinaline in combination with 80 mg/kg of gemcitabine. A second sub-group received the combination at a dose of 15 mg/kg/160 mg/kg. The third subgroup received the combination at a dose of 30 mg/kg acetyldinaline with 80 mg/kg of gemcitabine. The fourth sub-group received the combination of 45 mg/kg/80 mg/kg.

The data presented in FIGS. 2 and 4 establish that the combination of acetyldinaline and gemcitabine is surprisingly active in reducing the rate of growth of tumors in animals. The ability of these agents when used together establish the combination to be synergistic as an antitumor agent.

EXAMPLE 2

Because the synergistic effects observed with the combination of acetyldinaline and gemcitabine (shown in FIGS. 2 and 4) were so surprisingly dramatic, the experiment described above in Example 1 was repeated with additional doses of acetyldinaline. Table 1 below shows the activity of CI-994 and gemcitabine, alone and in combination, in the LC-12 mouse lung tumor model when tested according to the procedure of Example 1.

TABLE 1

Antitumor Effect of the Combination of CI-994 and Gemcitabine in the LC-12 Mouse Lung Tumor Model

| CI-994 | | Gemcitabine | | Toxic | % Weight | Antitumor Effect | | | |
|---|---|---|---|---|---|---|---|---|---|
| Dose[a] | Schedule | Dose[a] | Schedule | Deaths | Change[b] | CR[c] | PR[d] | T − C[e] | Net $Log_{10}$ Kill[f] |
| 7.5 | 11–15, 18–22, 25–29 | 0 | — | 0/6 | +4 | 1/6 | 0/6 | 2.4 | −1.2 |
| 15 | | 0 | — | 0/6 | +10 | 0/6 | 0/6 | 0.4 | −1.4 |
| 30 | | 0 | — | 0/6 | +1 | 0/6 | 0/6 | 1.6 | −1.3 |
| 60 | | 0 | — | 0/6 | −9 | 3/6 | 0/6 | 7.8 | −0.8 |
| 0 | — | 80 | 11, 14, 17, 20 | 0/6 | +1 | 1/6 | 0/6 | 15.4 | 0.5 |
| 0 | — | 160 | | 0/6 | −3 | 0/6 | 1/6 | 24.0 | 1.2 |
| 7.5 | 11–15, 18–22, 25–29 | 80 | 11, 14, 17, 20 | 0/6 | +8 | 2/6 | 0/6 | 23.5 | 0.4 |
| 15 | | 80 | | 0/6 | +7 | 2/6 | 1/6 | 23.8 | 0.5 |
| 30 | | 80 | | 0/6 | +8 | 5/6 | 0/6 | 37.0 | 1.5 |
| 60 | | 80 | | 3/6 | −8 | Toxic | Toxic | Toxic | Toxic |
| 7.5 | 11–15, 18–22, 25–29 | 160 | 11, 14, 17, 20 | 0/6 | −8 | 3/6 | 0/6 | 25.6 | 0.6 |
| 15 | | 160 | | 0/6 | −3 | 4/6 | 1/6 | 29.8 | 0.9 |
| 30 | | 160 | | 0/6 | −3 | 5/6 | 1/6 | >82.6 | >5.0 |
| 60 | | 160 | | 0/6 | — | Toxic | Toxic | Toxic | Toxic |

[a]Dose is in mg/kg/day.
[b]A weight loss is the maximum seen during treatment; a weight gain is the weight seen at the end of treatment.
[c]Complete response (CR) represents a tumor that could not be detected at the end of the study.
[d]Partial response (PR) represents a tumor that decreased by 50% or more during the study.
[e]The difference in days for the treated (T) and control (C) tumors to reach 750 mg.
[f]Net $log_{10}$ tumor cell kill was calculated from the T − C value.

The acetyldinaline was administered orally to each test group on Days 26–30, 33–37, and 40–44. Gemcitabine was administered IP on Days 10, 13, 16, and 19.

FIG. 4 shows that the tumors in the untreated controls started growing by the 11th day following implantation, and reached 750 mg (the "evaluation size") on Day 18. In contrast, tumors in animals treated with 15 mg/kg acetyldinaline and 80 mg/kg of gemcitabine showed very little growth until Day 35, and did not reach evaluation size until Day 42. Tumors in animals dosed with the 30 mg/kg/80 mg/kg combination started growing at Day 35, but did not reach the 750 mg evaluation size until Day 52. The tumors in animals dosed with the 30 mg/kg/160 mg/kg combination, as well as the 45 mg/kg/80 mg/kg combination, showed no growth, even at Day 75 when the test was ended.

EXAMPLE 3

The procedure of Example 1 was followed to evaluate the anti-tumor activity of combinations of CI-994 and cisplatin compared to the individual agents alone. The results are presented in Table 2. The table shows that treatment with 60 mg/kg/day of CI-994 caused two complete responses out of 10 test animals, while cisplatin alone at 2 mg/kg/day failed to cause any complete responses. The combination, however, caused a 70% complete response, namely complete responses in 7 out of 10 treated animals. The T-C effect was even more dramatic, going from 8.7 and 2.4 for the monotherapy treatments, to 84.2 for the combination treatment.

TABLE 2

Antitumor Effect of the Combination of CI-994 and Cisplatin in the LC-12 Mouse Lung Tumor Model

| CI-994 | | Gemcitabine | | Toxic | % Weight | Antitumor Effect | | | |
|---|---|---|---|---|---|---|---|---|---|
| Dose[a] | Schedule | Dose[a] | Schedule | Deaths | Change[b] | CR[c] | PR[d] | T − C[e] | Net Log$_{10}$ Kill[f] |
| 0 | — | 0 | — | 0/10 | +15 | 0/10 | 0/10 | — | — |
| 7.5 | 11–15, 18–22, 25–29 | 0 | — | 0/10 | +9 | 0/10 | 0/10 | −1.4 | 0 |
| 15 | | 0 | — | 0/10 | +11 | 0/10 | 0/10 | −1.9 | 0 |
| 30 | | 0 | — | 0/10 | +11 | 0/10 | 0/10 | 4.3 | −0.8 |
| 60 | | 0 | — | 0/10 | +11 | 2/10 | 0/10 | 8.7 | −0.5 |
| 0 | — | 1 | 11–15 | 0/10 | +13 | 0/10 | 0/10 | 2.6 | −0.1 |
| 0 | — | 1 | | 0/10 | +12 | 0/10 | 0/10 | 2.4 | −0.1 |
| 7.5 | 11–15, 18–22, 25–29 | 1 | 11–15 | 0/10 | +4 | 0/10 | 0/10 | 2.0 | −0.9 |
| 15 | | 80 | | 0/10 | +4 | 1/10 | 0/10 | 8.2 | −0.6 |
| 30 | | 80 | | 0/10 | +3 | 4/10 | 2/10 | 6.7 | −0.7 |
| 60 | | 80 | | 0/10 | +2 | 7/10 | 1/10 | 12.7 | −0.3 |
| 7.5 | 11–15, 18–22, 25–29 | 2 | 11–15 | 0/10 | +1 | 1/10 | 0/10 | 10.0 | −0.5 |
| 15 | | 2 | | 0/10 | −2 | 3/10 | 0/10 | 17.0 | −0.1 |
| 30 | | 2 | | 0/10 | −1 | 5/10 | 1/10 | 20.6 | 0.2 |
| 60 | | 2 | | 0/10 | −14 | 7/10 | 3/10 | 84.2 | 3.8 |

[a]Dose is in mg/kg/day.
[b]A weight loss is the maximum seen during treatment; a weight gain is the weight seen at the end of treatment.
[c]Complete response (CR) represents a tumor that could not be detected at the end of the study.
[d]Partial response (PR) represents a tumor that decreased by 50% or more during the study.
[e]The difference in days for the treated (T) and control (C) tumors to reach 750 mg.
[f]Net log$_{10}$ tumor cell kill was calculated from the T − C value.

EXAMPLE 4

The general procedure of Example 1 was followed to evaluate CI-994 and capecitabine, alone and in combination, against a colon tumor. The assay was carried out the same as described in Example 1, except that a fragment of C26 colon tumor was surgically implanted into the mice, instead of the LC-12 lung tumor which was used in the foregoing examples. Table 3 reports the results of monotherapy with specific doses of CI-994, and with capecitabine (Xeloda™), and with combination therapy wherein the animals were first dosed with capecitabine (on Days 3–7 and 10–14), followed by dosing with CI-994 (on Days 17-21, 24-28, and 31-35).

The data in Table 3 establish that none of the animals receiving CI-994 alone were tumor free at the end of the assay, that 30% (3 out of 10) of the animals receiving capecitabine alone were tumor free, and that 70% (7 out of 10) animals receiving the combination of CI-994 plus capecitabine were tumor free.

Table 4 presents the results of the same assay, except that the combination agents, CI-994 and capecitabine, both were administered simultaneously on Days 3–7 and 10–14. Dosing with CI-994 was continued on Days 17–21, whereas capecitabine therapy was stopped at Day 14.

TABLE 3

Antitumor Effect of the Combination of CI-994 and Xeloda in the C26 Mouse Colon Tumor Model:
Effect of Treatment with Xeloda Followed by Treatment with CI-994 against Early Stage Tumor

| CI-994 | | Xeloda | | Toxic | % Weight | Antitumor Effect | | | | |
|---|---|---|---|---|---|---|---|---|---|---|
| Dose[a] | Schedule | Dose[a] | Schedule | Deaths | Change[b] | CR[c] | PR[d] | T − C[e] (add.) | Net Log$_{10}$ Kill[f] | % Tumor free |
| 7.5 | 17–21, 24–28, 31–35 | 0 | — | 0/10 | −5 | Early Stage | Early Stage | 3.1 | −1.3 | 0/10 |
| 15 | | 0 | — | 0/10 | −9 | Early Stage | Early Stage | 6.7 | −1.0 | 0/10 |
| 30 | | 0 | — | 1/10 | −16 | Early Stage | Early Stage | 8.4 | −0.8 | 0/10 |
| 60 | | 0 | — | 0/10 | −10 | Early Stage | Early Stage | 10.1 | −0.7 | 0/10 |
| 0 | — | 500 | 3–7, 10–14 | 0/10 | −0.2 | Early Stage | Early Stage | 13.8 | 0.2 | 2/10 |
| 0 | — | 750 | | 1/10 | −18 | Early Stage | Early Stage | 20.7 | 0.8 | 3/10 |
| 7.5 | 17–21, 24–28, 31–35 | 500 | 3–7, 10–14 | 0/10 | −1 | Early Stage | Early Stage | 13.7 (16.9) | −0.4 | 3/10 |
| 15 | | 500 | | 0/10 | −1 | Early Stage | Early Stage | 17.3 (20.5) | −0.1 | 4/10 |
| 30 | | 500 | | 0/10 | −4 | Early Stage | Early Stage | 18.3 (22.2) | 0.0 | 3/10 |
| 60 | | 500 | | 0/10 | −4 | Early Stage | Early Stage | 20.4 (23.9) | 0.2 | 6/10 |
| 7.5 | 17–21, 24–28, 31–35 | 750 | 3–7, 10–14 | 1/10 | −13 | Early Stage | Early Stage | 19.1 (23.8) | 0.1 | 4/10 |
| 15 | | 750 | | 2/10[g] | −15 | Early Stage | Early Stage | 29.8 (27.1) | 0.4 | 2/10 |

TABLE 3-continued

Antitumor Effect of the Combination of CI-994 and Xeloda in the C26 Mouse Colon Tumor Model:
Effect of Treatment with Xeloda Followed by Treatment with CI-994 against Early Stage Tumor

| CI-994 | | Xeloda | | Toxic | % Weight | Antitumor Effect | | | | |
|---|---|---|---|---|---|---|---|---|---|---|
| Dose[a] | Schedule | Dose[a] | Schedule | Deaths | Change[b] | CR[c] | PR[d] | T − C[e] (add.) | Net Log$_{10}$ Kill[f] | % Tumor free |
| 30 | | 750 | | 1/10 | −10 | Early Stage | Early Stage | 45.0 (29.1) | 2.3 | 7/10 |
| 60 | | 750 | | 6/10 | Toxic | Early Stage | Early Stage | Toxic | Toxic | Toxic |

[a]Dose is in mg/kg/day.
[b]A weight loss is the maximum seen during treatment; a weight gain is the weight seen at the end of treatment.
[c]Complete response (CR) represents a tumor that could not be detected at the end of the study. This was an early stage test; therefore, CRs couldn't be calculated.
[d]Partial response (PR) represents a tumor that decreased by 50% or more during the study. This was an early stage test; therefore, PRs couldn't be calculated.
[e]The difference in days for the treated and control tumors to reach 750 mg. The values in parenthesis represent the T − C values for an additive antitumor effect.
[f]Net log$_{10}$ tumor cell kill was calculated from the T − C value.
[g]One death was assumed to be due to a gavage dosing error.

TABLE 4

Antitumor Effect of the Combination of CI-994 and Xeloda in the C26 Mouse Colon Tumor Model:
Effect of Simultaneous Treatment with CI-994 and Xeloda Against Early Stage Tumor

| CI-994 | | Xeloda | | Toxic | % Weight | Antitumor Effect | | | | |
|---|---|---|---|---|---|---|---|---|---|---|
| Dose[a] | Schedule | Dose[a] | Schedule | Deaths | Change[b] | CR[c] | PR[d] | T − C[e] (add.) | Net Log$_{10}$ Kill[f] | % Tumor free |
| 7.5 | 3–7, 10–14, 17–21 | 0 | — | 0/10 | +5 | Early Stage | Early Stage | 1.6 | −2.2 | 0/10 |
| 15 | | 0 | — | 0/9 | −8 | Early Stage | Early Stage | 1.0 | −2.3 | 0/9 |
| 30 | | 0 | — | 0/9 | −11 | Early Stage | Early Stage | 4.6 | −1.8 | 0/9 |
| 60 | | 0 | — | 0/9 | −12 | Early Stage | Early Stage | 4.8 | −1.8 | 0/9 |
| 0 | — | 500 | 3–7, 10–14 | 0/10 | +2 | Early Stage | Early Stage | 15.2 | 0.6 | 0/10 |
| 0 | — | 750 | | 0/10 | −12 | Early Stage | Early Stage | 20.4 | 1.3 | 1/10 |
| 7.5 | 3–7, 10–14, 17–21 | 500 | 3–7, 10–14 | 0/10 | +6 | Early Stage | Early Stage | 15.4 (16.8) | −0.4 | 0/10 |
| 15 | | 500 | | 0/10 | +6 | Early Stage | Early Stage | 14.5 (16.2) | −0.5 | 1/10 |
| 30 | | 500 | | 0/10 | −11 | Early Stage | Early Stage | 14.2 (19.8) | −0.5 | 0/10 |
| 60 | | 500 | | 0/10 | −8 | Early Stage | Early Stage | 18.1 (20.0) | 0.0 | 1/10 |
| 7.5 | 3–7, 10–14, 17–21 | 750 | 3–7, 10–14 | 0/10 | −11 | Early Stage | Early Stage | 19.1 (22.0) | 0.2 | 0/10 |
| 15 | | 750 | | 0/10 | −7 | Early Stage | Early Stage | 16.9 (21.4) | −0.2 | 2/10 |
| 30 | | 750 | | 0/10 | −14 | Early Stage | Early Stage | 17.4 (25.0) | −0.1 | 0/10 |
| 60 | | 750 | | 1/10 | −18 | Early Stage Early Stage | Early Stage | 16.4 (25.2) | −0.2 | 0/10 |

[a]Dose is in mg/kg/day.
[b]A weight loss is the maximum seen during treatment; a weight gain is the weight seen at the end of treatment.
[c]Complete response (CR) represents a tumor that could not be detected at the end of the study. This was an early stage test; therefore, CRs couldn't be calculated.
[d]Partial response (PR) represents a tumor that decreased by 50% or more during the study. This was an early stage test; therefore, PRs couldn't be calculated.
[e]The difference in days for the treated and control tumors to reach 750 mg. The values in parenthesis represent the T − C values for an additive antitumor effect.
[f]Net log$_{10}$ tumor cell kill was calculated from the T − C value.

EXAMPLE 5

The combinations of CI-994 plus gemcitabine, and of CI-994 plus cisplatin, were evaluated in human ovarian carcinoma cells, and the data was analyzed according to the Chou and Talalay program which established both combinations to be synergistic.

Ovcar-4 Human Ovarian

Figure 5:
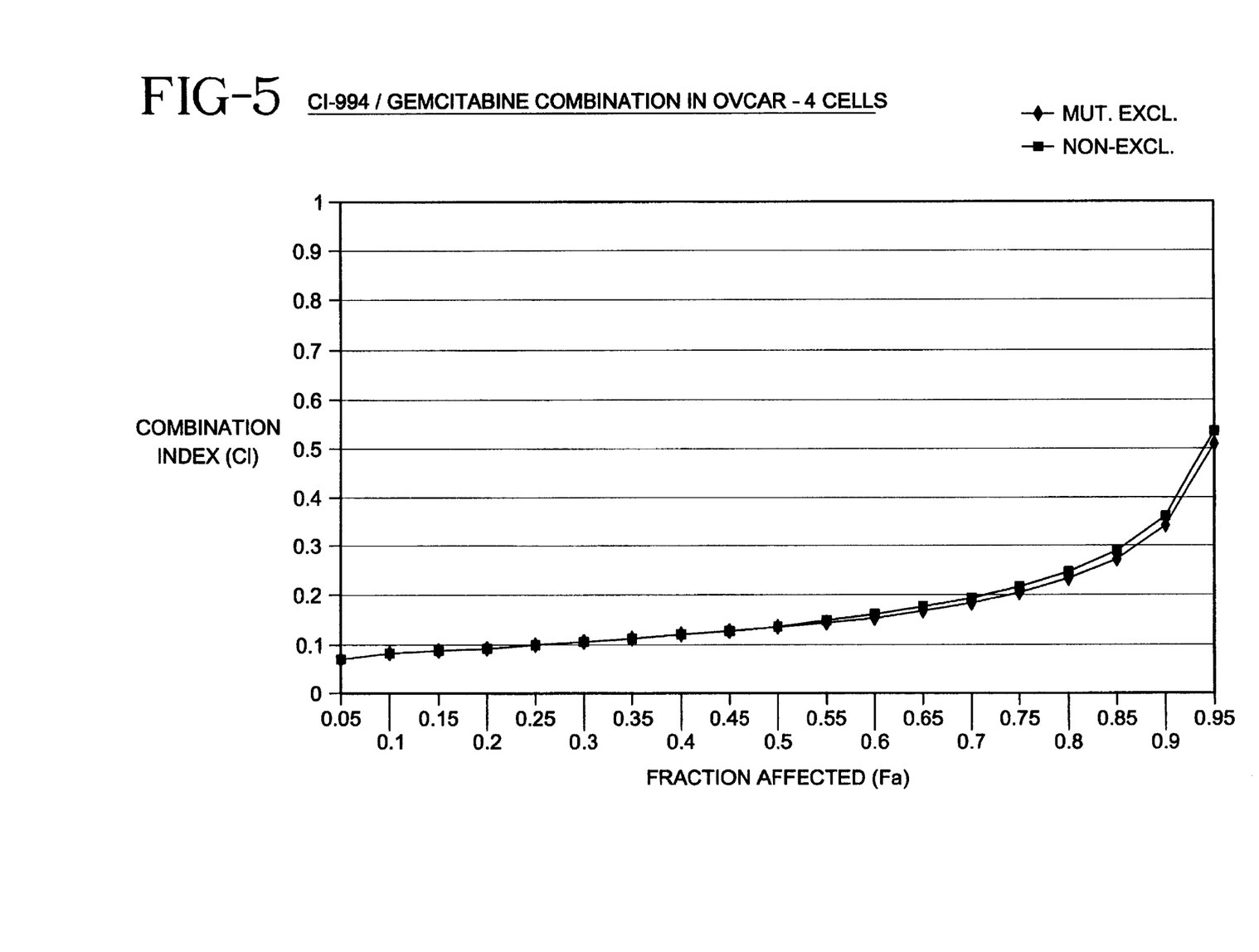
FIG. 5 shows the synergy of CI-994 and gemcitabine in human ovarian carcinoma cells.
Figure 6:
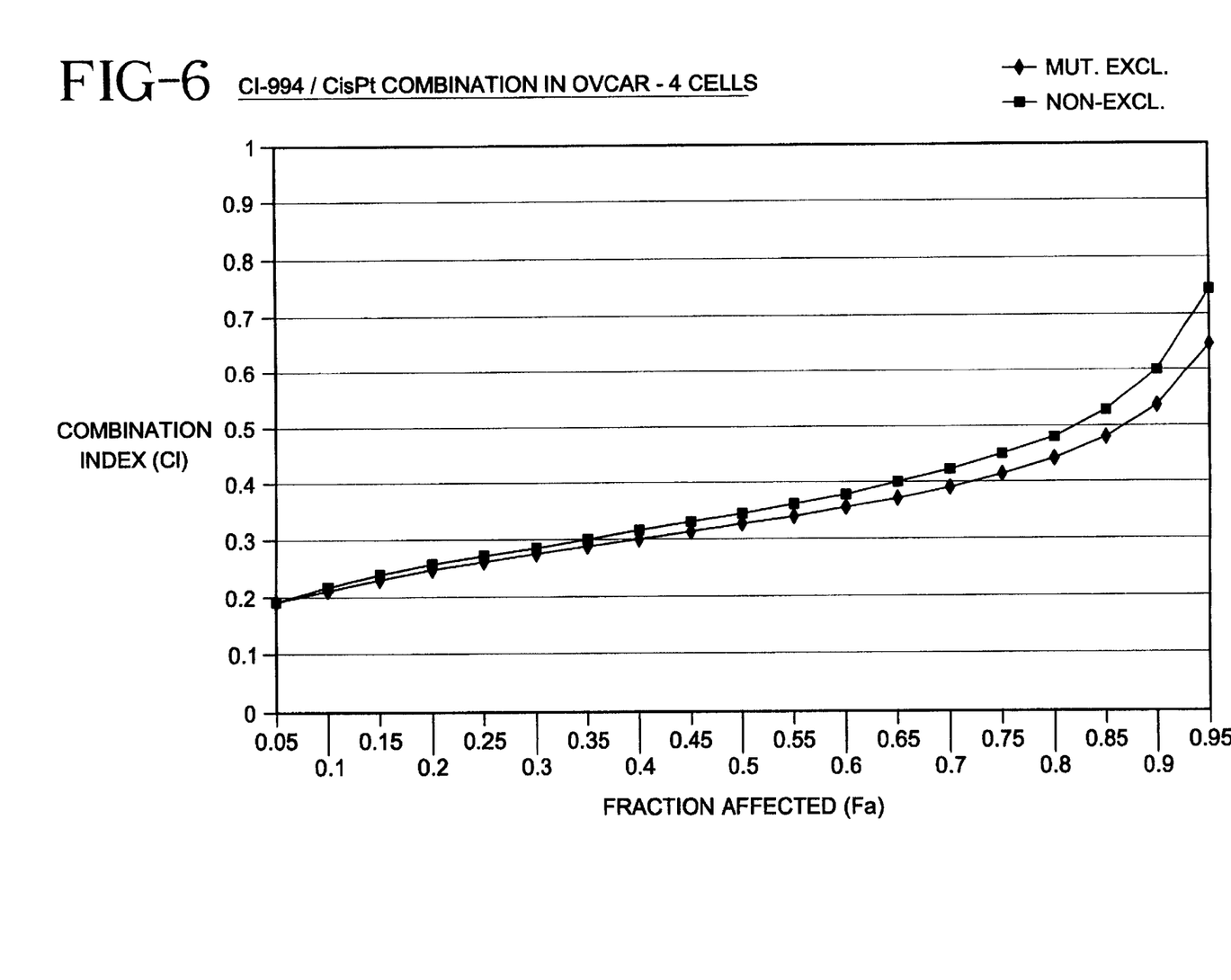
FIG. 6 shows the synergy of CI-994 and cisplatin in human ovarian carcinoma cancer.

Ovcar-4 human ovarian carcinoma cells were seeded into 96-well culture plates in RPMI 1640 culture media supplemented with 20% fetal calf serum and 10 μg/mL of insulin. Various concentrations of CI-994 and either cisplatin or gemcitabine were added together 24 hours after cells were initially seeded into the culture plates and allowed to attach. The effect of CI-994, gemcitabine or cisplatin alone and in combination on Ovcar-4 proliferation was determined after 96 hours of incubation at 37° C. using the SRB assay as previously described (Skehan P., Stoneng R, Scudiero D, et al. New calorimetric cytotoxicity assay for anticancer-drug screening. *J Natl. Cancer Inst.* 1990;82:1 107–1112). The combination chemotherapy data was analyzed using the Biosoft program, "Dose Effect Analysis with Microcomputers for IBM PC", which is a standard program for quantifying synergism, additivism, and antagonism among anticancer agents, and is based on the median-effect principle of mass-action law using an enzyme kinetic system model described by Chou and Talalay. Plots of fraction affected (Fa) versus combination index (CI) are called Fa-CI plots. These plots indicate synergism, additivity, or antagonism of 2 drugs at various effect levels in a mixture that is serially diluted. If several mixture are made, it is possible to estimate the optimal combination ratio for maximal synergy. Different effect levels usually give different degrees of synergism, additivism, or antagonism. CI values <1 indicate synergism; CI values >1 indicate antagonism and values that hover around 1 as a straight line indicate additivity. FIGS. 5 and 6 show representative Fa-CI plots for CI-994 plus gemcitabine (FIG. 5), and CI-994 plus cisplatin (FIG. 6). In both plots, CI values over the entire Fa range are less than one, indicating synergy for the drug combinations.

CLINICAL EVALUATION OF COMBINATION THERAPY

This is a multicenter, open-label Phase 1 study of CI-994 given in combination with gemcitabine to patients with advanced solid tumors.

The objectives of this study are to determine the, (1) maximum tolerated dose (MTD), (2) recommended Phase 2 dose, (3) pharmacokinetics, (4) safety profile, and (5) to observe for antitumor activity of CI-994 when given in combination with gemcitabine to patients with advanced solid tumors. The primary efficacy endpoint is the attainment of either a partial response (PR) or a complete response (CR). Secondary endpoints include time to PR or CR, duration of PR or CR, and survival.

Gemcitabine is administered as a 30-minute intravenous infusion on Days 1,8, and 15 of a 28-day treatment course, using an initial dose of 1000 mg/m$^2$. CI-994 is administered orally as a daily dose for 21 days of a 28-day course, beginning on Day 1. Patients may receive subsequent courses of treatment based on individual tolerance and response to therapy. Patients whose disease does not respond or who develop intolerable adverse events are discontinued from study treatment.

The initial dose level of CI-994 is 4 mg/m$^2$. A minimum of 3 patients will be treated at each dose level, Dose levels are increased by 2 mg/m$^2$ until the MTD is reached. Ten additional patients are to be treated at the dose level recommended for Phase 2 studies, which is expected to be the MTD or one dose level below the MTD.

Once a patient begins study treatment, the addition of other cancer treatment will confound the assessment of safety and efficacy and therefore is not allowed. This restriction precludes the addition of systemic cytotoxic, hormonal, immunologic, or other biologic agents while the patient is in the treatment phase of this protocol. Patients who require palliative radiotherapy while on study are generally considered to have progressive disease and, unless compelling information exists to the contrary, are to be discontinued from study medication. Patients who develop new brain metastases while on study may have treatment interrupted to receive a course of cranial irradiation, then be restarted on study medication after a recovery period of at least 1 week.

Antiemetics may be used at the investigator's discretion for prevention and/or treatment of nausea or vomiting. Every effort should be made to ensure nausea and vomiting is controlled, as these conditions may preclude a patient from taking or absorbing the oral doses of CI-994, This issue is particularly relevant on Days 1, 8, and 15, when gemcitabine is also administered. Because CI-994 caused sedation and somnolence at higher doses in the Phase 1 program, antiemetics that are least likely to cause these side effects should be used.

Colony-stimulating factors may be used at the investigator's discretion to treat episodes of severe myelosuppression that are complicated by infection, but should otherwise not be used to support low blood counts or to maintain dose intensity, If criteria are met for a Complete Response (CR), administer 2 additional courses of treatment beyond confirmation of the CR and then completely reassess the patient's disease state. If the patient is considered to be clinically free of disease at that time, discontinue the gemcitabine and continue to administer CI-994 for 3 additional months, using the same dose and schedule (3 weeks on/1 week off). At that time, again completely reassess the patient's disease state. If the patient is still in CR, the investigator must evaluate the risks and potential benefits of continuing CI-994 treatment.

Treatment Courses

A treatment course consists of gemcitabine given intravenously on Days 1, 8, and 15 of a 28-day course plus CI-994 administered daily orally, beginning on Day 1, for 21 days of a 28-day course. Courses are to be repeated on Day 29 if there has been adequate recovery from adverse events and myelosuppression, defined as nonhematologic parameters of Grade $\leq 1$, platelet count $\geq 100,000/\mu L$, and absolute neutrophil count $\geq 1500/\mu L$. Subsequent courses may be delayed by weekly intervals up to 3 weeks. If recovery has not occurred by Day 50, the patient is to be discontinued from study medication.

Gemcitabine Dosing

The initial dose of gemcitabine in each course is 1000 mg/m$^2$, (given as a 30-minute intravenous infusion. Dose adjustments may be required during a treatment course. Follow the manufacturer's recommendations for information regarding preparation and administration.

CI-994 Dose Levels

CI-994 doses are calculated based on body surface area (BSA) and must then be rounded to the closest available capsule strength. CI-994 is available in capsule strengths of 2.5, 5, and 25 mg. Doses may be taken without regard to meals.

The initial CI-994 dose level is 4 mg/m$^2$. Subsequent dose levels will be increased (or decreased if necessary) by a fixed increment of 2 mg/m$^2$ until the MTD is determined. Individual patients may not receive dose escalations of gemcitabine or CI-994 in subsequent courses. Patients may receive a lower dose of CI-994 in a subsequent course if dose-limiting toxicities were experienced.

Three new patients will be assessed at each new dose level. The minimum time that these patients must be followed is 4 weeks before a new dose level may be opened (unless treatment was interrupted earlier and the patient is recovering from adverse events). If none of these 3 patients experience a dose-limiting toxicity, the next higher dose level will be opened. If one patient develops a dose-limiting toxicity, 3 more patients will be enrolled at that dose level. If $\geq 2$ of 6 patients experience a dose-limiting toxicity at the same level, that dose level will be considered the MTD.

An assessable patient is defined as one who received 3 weekly doses of gemcitabine plus at least 80% of the CI-994 doses ($\geq 17$ doses), or a patient whose treatment course was discontinued early or was noncompliant (<17 doses) due to treatment-related adverse events. A patient who took fewer than 17 doses of CI-994 or did not complete the treatment course because of nontreatment-related reasons (eg, missed appointments, ran out of CI-994 supplies, developed a coexisting medical condition that rendered the patient unable to swallow capsules, developed rapidly progressing disease) is not considered to be an assessable patient for the tolerability of that dose level.

Patients should be encouraged to take their CI-994 dose at approximately the same time each day. However, a variance of up to 12 hours either way is allowed for any given dose, rather than miss a day's dose. If a patient misses a day's dose entirely, they must be instructed not to 'make it up'the next day. If a patient vomits anytime after taking a dose of CI-994, they must be instructed not to 'make it up', but to resume subsequent doses the next day as prescribed.

On Days 1, 8, and 15, the CI-994 dose should be given 2 hours before the gemcitabine dose, to ensure maximal absorption in the event the patient develops vomiting following the gemcitabine dose.

Once the MTD is determined, 10 additional patients will be treated at the Phase 2 dose level, which is expected to be the MTD or one dose level below the MTD.

Dose Adjustments During a Course

Continuation of gemcitabine and CI-994 during a course is dependent on patient tolerance and hematologic parameters. Reduced doses of gemcitabine may be required on Days 8 and 15, as recommended by the manufacturer and shown in the table below. The dose of CI-994 is not to be increased or decreased during a treatment course, although early termination may be required as described below. If both study medications must be stopped before a course is completed, do not complete that course, but instead follow the patient for recovery, then start another course using a reduced dose of CI-994.

| Condition | Dose Adjustments During a Treatment Course | |
| --- | --- | --- |
| | % Full Dose of Gemcitabine | % Full Dose of CI-994 |
| Absolute Neutrophil Count/$\mu$L | | |
| $\geq$1000 | 100 | 100 |
| $\geq$500 to 999 | 75 | 100 |
| <500 | 0 | 0 |
| - OR - | | |
| Platelet Count/$\mu$L | | |
| $\geq$100,000 | 100 | 100 |
| $\geq$50,000 to 99,000 | 75 | 100 |
| <50,000 | 0 | 0 |
| - OR - | | |
| Treatment-Related Nonhematologic Toxicity | | |
| Grade 0–2 | 100 | 100 |
| Grade 3 or 4 | 0 | 0 |

Gemcitabine dose adjustments shown in the table above are based on the results on that day. For example, on Day 8 draw a CBC and check the results. Determine if dosing is to continue. If so, have the patient take the CI-994 dose. Two hours later, give the gemcitabine dose which, if necessary, has been reduced.

The decision to discontinue CI-994 dosing during a course is based on adverse events or hematology results at any time. Example: A patient has a platelet count on Day 11 of 45,000/$\mu$L. Instruct the patient to stop taking CI-994 capsules (and to return all study medication containers to the site). Obtain another CBC on Day 15. If the platelet count on Day 15 is 50,000 to 99,000/$\mu$L, administer 75% of the calculated gemcitabine dose but do not reinstitute CI-994 dosing. If the platelet count on Day 15 remains below 50,000/$\mu$L, do not retreat with gemcitabine. Consider this course to be terminated and follow the patient for recovery. In either case, the patient may receive a subsequent treatment course using the same initial dose of gemcitabine (1000 mg/m$^2$) and a CI-994 dose that has been reduced by 2 mg/m$^2$.

Drug Formulation and Stability

Gemcitabine is to be obtained by the site from commercial sources. Follow the manufacturer's recommendation for preparation, administration, stability, and storage conditions.

CI-994 is formulated in identically appearing gelatin capsules containing 2.5, 5, or 25 mg of study medication, plus inactive ingredients of lactose, cornstarch, and talc or polyethylene glycol 6000. Store at controlled room temperature.

The foregoing data establish an unexpectedly favorable interaction between acetyldinaline and gemcitabine, and between acetyldinaline and cisplatin. Accordingly, this invention provides a method of treating susceptible neoplasms comprising administering acetyldinaline in a regimen together with either gemcitabine, a pharmaceutically acceptable salt thereof, or cisplatin. The combination generally will include each active ingredient packaged separately, thereby avoiding any interaction between the agents prior to administration. If desired, the individually packaged drugs can be placed in a single carton as a kit, thereby providing convenience to the attending physician or medical attendant The susceptible neoplasms to be treated according to this invention include solid tumors, especially advanced solid tumors and nonsmall cell lung cancer, as well as renal cell cancer, pancreatic cancer, head and neck cancer, ovarian cancer, myeloma, prostate cancer, and breast cancer.

What is claimed is:

1. A combination of antineoplastic agents comprising an antitumor amount of acetyldinaline and an antitumor amount of gemcitabine, a pharmaceutically acceptable salt thereof, capecitabine, or cisplatin.

2. A combination of claim 1 comprising acetyldinaline formulated as a capsule.

3. A combination of claim 2 comprising gemcitabine or a pharmaceutically acceptable salt thereof formulated as a sterile solution for intravenous infusion.

4. A combination of claim 3 comprising gemcitabine monohydrochloride.

5. A combination of claim 3 comprising gemcitabine monohydrobromide.

6. A method of treating cancer comprising administering to an animal in need of treatment an antitumor amount of a combination of claim 1.

7. A. method of claim 6 wherein the cancer treated is nonsmall cell lung cancer.

8. A method of claim 7 comprising administering acetyldinaline in combination with gemcitabine monohydrochloride.

9. A method of claim 6 comprising administering acetyldinaline in combination with gemcitabine monohydrochloride.

10. A method of claim 6 wherein the cancer treated is a locally advanced (nonresectable Stage II or Stage III) or metastatic (Stage IV) adenocarcinoma of the pancreas.

11. A kit comprising acetyldinaline in one compartment and gemcitabine or a pharmaceutically acceptable salt thereof in a second compartment.

* * * * *